United States Patent
Clement et al.

(10) Patent No.: US 7,763,054 B2
(45) Date of Patent: Jul. 27, 2010

(54) VERTEBRAL OSTEOSYNTHESIS EQUIPMENT

(75) Inventors: Jean-Luc Clement, La Colle sur Loup (FR); Vincent Fiere, Lyons (FR); Jean Taylor, Cannes (FR); Yves Adam, Authie (FR); Bernard Villaret, Croix-Chapeau (FR)

(73) Assignee: Medicrea Technologies, La Rochelle (FR)

( * ) Notice: Subject to any disclaimer, the term of this patent is extended or adjusted under 35 U.S.C. 154(b) by 580 days.

(21) Appl. No.: 11/312,428

(22) Filed: Dec. 21, 2005

(65) Prior Publication Data

US 2006/0167455 A1    Jul. 27, 2006

Related U.S. Application Data

(63) Continuation-in-part of application No. PCT/IB2004/002371, filed on Jun. 24, 2004.

(60) Provisional application No. 60/490,518, filed on Jul. 29, 2003.

(30) Foreign Application Priority Data

Jun. 27, 2003   (FR) .................................. 03 07778

(51) Int. Cl.
*A61B 17/70* (2006.01)
(52) U.S. Cl. ..................................................... 606/265
(58) Field of Classification Search ......... 606/250–253, 606/264–267, 270, 272–275, 278
See application file for complete search history.

(56) References Cited

U.S. PATENT DOCUMENTS

| | | | | |
|---|---|---|---|---|
| 5,613,968 A | * | 3/1997 | Lin ............................ | 606/320 |
| 5,810,817 A | * | 9/1998 | Roussouly et al. .......... | 606/250 |
| 6,050,997 A | | 4/2000 | Mullane | |
| 6,123,706 A | * | 9/2000 | Lange ......................... | 606/264 |
| 6,267,765 B1 | * | 7/2001 | Taylor et al. ............... | 606/86 A |
| 6,673,074 B2 | * | 1/2004 | Shluzas ...................... | 606/278 |
| 7,104,992 B2 | * | 9/2006 | Bailey ........................ | 606/278 |
| 2003/0028191 A1 | | 2/2003 | Shluzas | |
| 2006/0229606 A1 | * | 10/2006 | Clement et al. ............... | 606/61 |
| 2007/0072493 A1 | * | 3/2007 | Sournac et al. ............. | 439/715 |
| 2007/0100339 A1 | * | 5/2007 | Clement et al. ............... | 606/61 |
| 2007/0149973 A1 | * | 6/2007 | Clement et al. ............... | 606/61 |
| 2007/0161987 A1 | * | 7/2007 | Capote et al. ................. | 606/61 |
| 2007/0173817 A1 | * | 7/2007 | Sournac et al. ............... | 606/61 |

FOREIGN PATENT DOCUMENTS

| | | |
|---|---|---|
| FR | 2 743 290 | 7/1997 |
| FR | 2 832 620 | 5/2003 |

* cited by examiner

*Primary Examiner*—Eduardo C Robert
*Assistant Examiner*—Ellen C Hammond
(74) *Attorney, Agent, or Firm*—Young & Thompson

(57) ABSTRACT

Equipment includes bony anchoring members one or two linking rods, intended to be connected to the anchoring members, and parts for connecting the linking rod(s) to the anchoring members, at least one anchoring member including a proximal threaded stud and a clamping element for assembling a connecting part thereon, the connecting part including a clamping element for immobilizing the linking rod with respect thereto. The connecting part includes a rounded section for hugging a linking rod and two parallel branches having holes enabling engagement on the proximal threaded stud of the anchoring member; and the clamping elements may be engaged coaxially on the proximal threaded stud of the anchoring member, a first clamping element enabling the assembly of the connecting part on this proximal threaded stud and the second clamping element enabling to clamp both branches of this connecting part.

19 Claims, 3 Drawing Sheets

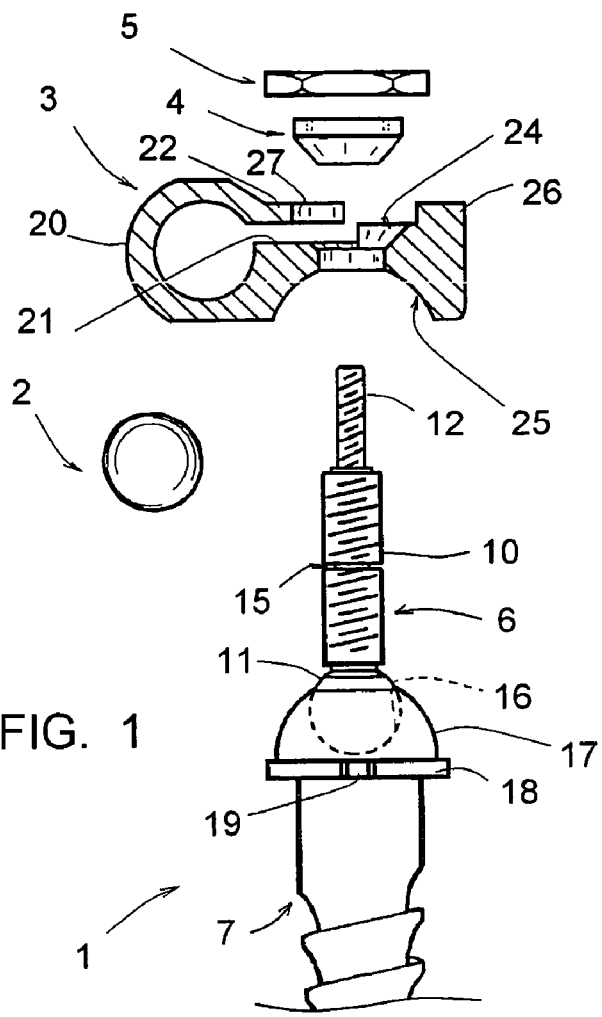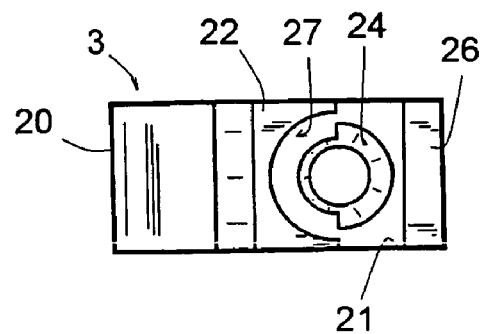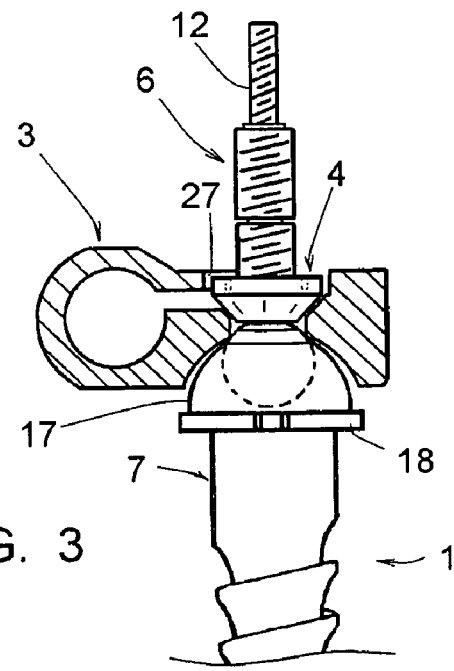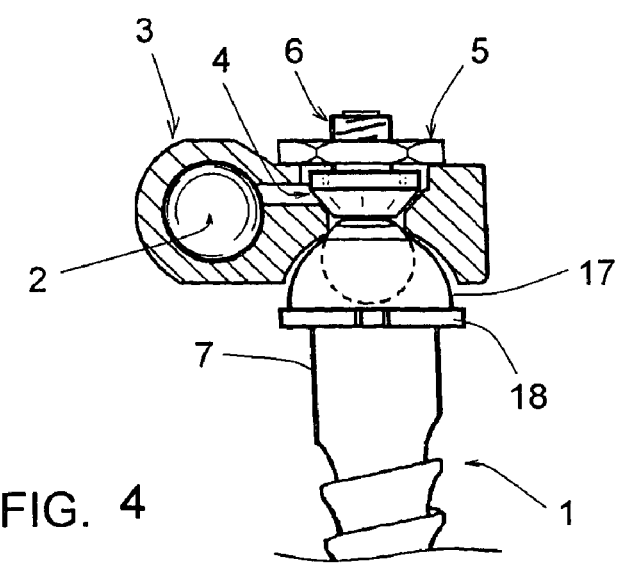

VERTEBRAL OSTEOSYNTHESIS EQUIPMENT

This patent application claims the priorities to:
FR 03 07778, filed on Jun. 27, 2003;
U.S. Provisional application No. 60/490,518, filed on Jul. 29, 2003.

BACKGROUND OF THE INVENTION

1. Field of the Invention

The present invention relates to a vertebral osteosynthesis equipment.

2. Description of the Related Art

A vertebral osteosynthesis equipment generally includes bony anchoring members, such as pedicular screws or hooks, one or two linking rods, intended to be connected to these anchoring members and to be attached to the vertebrae by dint thereof, and parts for connecting this (these) linking rod(s) to these anchoring members. The equipment may also comprise length-adjustable crossbeams, which link transversally two parallel linking rods in order to hold said rods with respect to one another.

In an existing type of equipment, each anchoring member comprises a proximal threaded stud whereon a nut may be screwed, and each connecting part comprises a rounded section intended for surrounding a linking rod and two parallel branches drilled with holes. These branches are intended for engaging onto said proximal stud and for being clamped, by means of that nut, against a bearing surface provided on the anchoring member, said operation enabling to clamp said rounded section around the linking rod and thereby ensuring longitudinal immobilisation of this rod with respect to the anchoring member. The anchoring members may be of "monoaxial" type, i.e. comprise a proximal threaded stud integral with the base portion of the anchoring member serving for bony anchoring, or may be of "polyaxial" type, i.e. comprise a proximal threaded stud articulated with respect to that base portion.

When installing the equipment, the anchoring member(s) are placed on the vertebrae, then extension pieces are engaged on the proximal studs of these anchoring members. The connecting parts, with the rod(s) engaged in their rounded portions, are then engaged on these extension pieces and run down along the latter until they rest on the anchoring members. The extension pieces are then withdrawn and the clamping nuts are placed.

To enable adequate correction of the position of the vertebrae, the linking rod(s) must be shaped in one or several planes. This operation leads to successive trials until the adequate form is obtained. Successive insertions and retractions of the extension pieces and successive running down operations of the assemblies composed of connecting parts—linking rods along the latter, then withdrawing the extension pieces for placing the nuts, are then relatively tedious and time-consuming operations.

Moreover, with polyaxial anchoring members, the movements of the proximal studs modify the positions of the connecting parts and disturb consequently the determination of the form which should be given to the linking rod(s) so that these rods may be engaged in these connecting parts, which disturbs noticeably the installation of the equipment.

It is besides known by the documents US 2003/028191 or U.S. Pat. No. 6,050,997 to provide a single-branch connecting part, with a closed housing for receiving the linking rod, fitted with a screw, this screw enabling to clamp the linking rod in this housing.

This connecting part structure is assessed as non-optimal, from the handiness viewpoint of the equipment at installation as from the viewpoint of the clamping obtained.

SUMMARY OF THE INVENTION

The purpose of the present invention is to remedy the shortcomings of existing equipment, by providing vertebral osteosynthesis equipment noticeably easier and quicker to be implanted than any extent equipment.

Another object of the invention is to provide a piece of equipment enabling to facilitate noticeably the determination of the form to confer to the linking rod(s).

An additional object of the invention is to provide a piece of equipment enabling perfect clamping of a linking rod, as resistance to the repeated loads inflicted to this type of equipment.

The equipment affected includes, in itself, bony anchoring members, such as pedicular screws or hooks, one or two linking rods, intended to be connected to these anchoring members and to be attached to the vertebrae by dint thereof, and parts for connecting this (these) linking rod(s) to these anchoring members, at least one anchoring member including a proximal threaded stud and a clamping means for assembling a connecting part thereon, and this connecting part including a clamping means for immobilising the linking rod with respect thereto.

According to the invention, said connecting part comprises a rounded section intended for hugging a linking rod and two parallel branches drilled with holes enabling engagement on the proximal threaded stud of said anchoring member, these two branches being laid out for being clamped in order to clamp said rounded section around the linking rod; and said clamping means may be engaged coaxially on the proximal threaded stud of said anchoring member, a first clamping means enabling the assembly of the connecting part on this proximal threaded stud and the second clamping means enabling to clamp both branches of this connecting part.

Both these clamping means enable to facilitate noticeably the determination of the form to confer to the linking rod(s) and to make the equipment noticeably easier and quicker to be implanted than any extent equipment, while enabling perfect clamping of a linking rod, as resistance to the repeated loads inflicted to this type of equipment.

According to an embodiment of the invention, the proximal branch of the connecting part, i.e. the furthermost from the vertebrae after implantation, comprises a hole for letting said first clamping means therethrough, so that said first clamping means rests, when screwed on said proximal threaded stud, solely on the distal branch of the connecting part, and said second clamping means exhibits a diameter greater than that of this hole, so that said second clamping means rests, when screwed on said proximal threaded stud, on the proximal branch of the connecting part, thereby clamping both branches and therefore immobilising the linking rod.

This connecting part may thus be clamped on the anchoring member by dint of said first clamping means without clamping the branches of the connecting part, therefore with the possibility of placing and retracting the linking rod. The connecting part may therefore be placed on the anchoring member in its final position, before the linking rod is formed as requested.

According to another embodiment of the invention,
the hole of the distal branch of the connecting part, i.e. the closest of the vertebrae after implantation, is tapered;
said second clamping means is in the form of a tubular screw, which may be screwed in the hole of the distal branch and rest against the proximal branch for clamping both branches, the axial bore of this screw having a diameter greater than that of the proximal threaded stud so as not to oppose the engagement of the connecting part, thus equipped with said second clamping means, on the proximal threaded stud, and
said first clamping means is in the form of a nut which may rest against the head of the screw formed by said second clamping means, for assembly of the connecting part on the proximal threaded stud.

The connecting part according to this embodiment may therefore be clamped on the linking rod then may be engaged on the proximal threaded stud of an anchoring member and be installed on this anchoring member.

According to still another embodiment of the invention,
the proximal branch of the connecting part is shorter than the distal branch and comprises a scalloping at of its free end;
the first and second clamping means comprise nuts which may be screwed on the proximal stud of the corresponding anchoring member, said scalloping having dimensions greater than that the nut which is part of said first clamping means, to enable this nut to rest, when being clamped, against the distal branch and to clamp this branch against the proximal zone of the portion of the anchoring member engaged with the vertebra until the connecting part is locked with respect to said proximal stud, and said scalloping having dimensions smaller than those of the nut which is part of said seconds clamping means, to enable this nut to rest, when being clamped, against the proximal branch and to bring both branches closer to one another in order to immobilise the linking rod in said rounded section of the connecting part.

BRIEF DESCRIPTION OF THE DRAWING FIGURES

The invention will be better understood, and other characteristics and advantages thereof will appear, with reference to the appended schematic drawings, representing, for non-limiting exemplification purposes, several possible embodiments of parts included in the equipment affected.

FIG. 1 is a partial view of a polyaxial pedicular screw, of a linking rod seen from its end, of a connecting part in cross-section and of two nuts included in such equipment, according to a first embodiment;

FIG. 2 is a view of the connecting part, from above;

FIG. 3 is a view of the screw and of the connecting part similar to FIG. 1, after assembly of a first nut;

FIG. 4 is a view similar to FIG. 3, after assembly of the second nut;

DETAILED DESCRIPTION OF THE PREFERRED EMBODIMENTS

Figure 5:
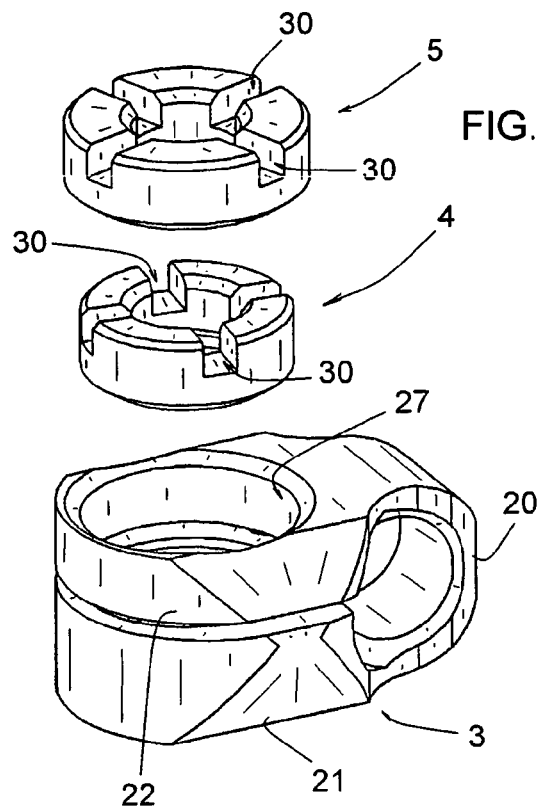
FIG. 5 is a perspective view of a connecting part and of two nuts according to a second embodiment.

The portions or elements of an embodiment which can be found identically or similarly in another embodiment will be designated, in the following description, by the same numeric references.

FIG. 1 represents a polyaxial pedicular screw 1, a rod 2 connecting several of these screws 1, a part 3 connecting this rod 2 to one of these screws 1 and two nuts 4, 5 enabling to assemble the linking rod 2 to this screw 1.

The screw 1 comprises a proximal threaded stud 6 and threaded distal screw body 7. The stud 6 is intended for receiving the part 3 engaged thereon and the nuts 4, 5 screwed thereon while the body 7 is intended for insertion into the pedicula of a vertebra.

The stud 6 exhibits a threaded cylindrical portion 10, a spherical distal head 11 and a threaded proximal rod 12.

The portion 10 exhibits a zone 15 of reduced diameter, enabling to break its proximal portion after placing and clamping nuts 4, 5, as appears by comparison of FIGS. 3 and 4.

The head 11 is intended for engaging into a proximal cavity 16 delineated by the proximal zone of the body 7 and for retention in this cavity by crimping a proximal wall 17 exhibited by this body 7. After crimping, the wall 17 is shaped into a hemispherical form. As shown on Figures, the dimensions of the cavity 16 and of the aperture delineated by the wall 17 after crimping to let through the stud 6 are such that a multidirectional backlash of this stud 6 with respect to the body 7 is possible.

The threaded rod 12 enables the assembly of an extension piece on the stud 6 by screwing, this extension piece enabling, once the screw 1 placed on the pedicula of a vertebra, to run down and to engage easily the connecting part 3 on this stud 6.

The body 7 comprises a proximal collar 18, intended for abutting against the pedicula of the vertebra. This collar 18 exhibits several radial notches 19, notably four notches at 90° to one another, for holding the body 7 in rotation when clamping the nuts 4 and 5.

The linking rod 2 is cylindrical and exhibits such rigidity as to hold several vertebrae with respect to one another. This rod 2 is however deformable in order to be shaped relative to the correction of the rachis to be performed.

The connecting part 3 comprises a rounded section 20 intended for hugging the linking rod 2 and two parallel lateral branches 21, 22.

The distal branch 21 is drilled with a hole for engaging the part 3 on the stud 6, this hole being extended, on its proximal side, by a conical pan 24 adapted to a conical portion of the nut 4.

The distal branch 21 exhibits moreover a hemispherical distal cavity 25, coaxial to said hole and of diameter greater than that of the wall 17. There exists thus a clearance between this wall 17 and the wall of the part 3 delineating the cavity 25, this clearance enabling angular orientation of the stud 6 with respect to the body 7.

At its free end, the distal branch 21 exhibits a proximal boss 26 against which the nut 5 rests when clamped, as shown on FIG. 4.

The proximal branch 22 is shorter than the distal branch 21 and comprises a scalloping 27 at its free end. As shown on FIGS. 2 and 3, this scalloping 27 has dimensions greater than those of the nut 4, to enable this nut 4 to engage into the pan 24 when being clamped, and to clamp this branch 21 against the wall 17 until the connecting part 3 is locked with respect to the stud 6 and immobilisation of this stud 6 with respect to the body 7. The scalloping 27 has moreover dimensions smaller than those of the nut 5, to enable this nut, during clamping, as shown on FIG. 4, to rest against the proximal branch 22 until abutting against the boss 26; this nut 5 thus enables to bring both branches 21, 22 closer to one another in order to immobilise the linking rod 2 in said rounded section 20 of the connecting part 3.

The nut 4 comprises proximal cavities provided around its axis, in order to be driven into rotation, for the clamping thereof, and the nut 5 is a hexagonal flat nut.

In practice, the number of screws 1 necessary to the treatment to be performed is placed in the pediculae of the vertebrae affected, then the extension pieces are screwed on the rods 12. The connecting parts 3, without the rod(s) 2 engaged in their rounded portions 20, and the nuts 4 and 5 are then engaged on these extension pieces and run down along the latter until the parts 3 rest on the walls 17.

The nuts 4 are then clamped in order to clamp the connecting parts 3 against the walls 17 and therefore immobilise these parts 3 and the studs 6 with respect to the body 7.

The rod(s) 2 are then shaped adequately relative to the vertebral correction to be performed, while taking into account the specific position of the parts 3, then this (these) rod(s) 2 are engaged through the portions 20 and the nuts 5 are clamped.

After retraction of the extension pieces, the studs 6 are cut off at tapered zones 15.

Figure 6:
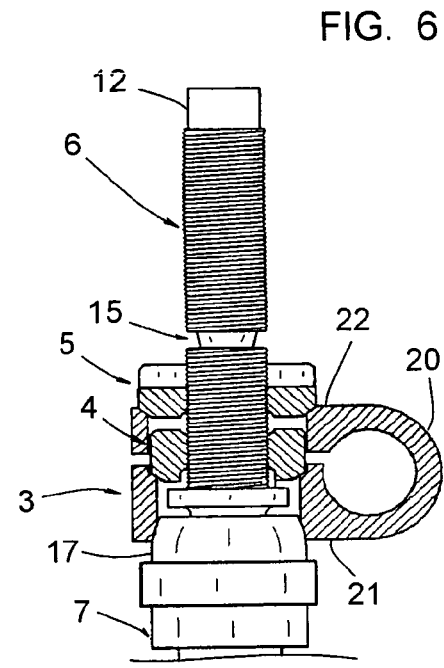
FIG. 6 is a sectional view thereof, as they are placed on an anchoring member.

FIGS. 5 and 6 show a connecting part 3 and two nuts 4, 5 according to the second embodiment.

In such a case, the nut 4 exhibits a circular external shape and has an external diameter smaller than that of the hole 27 of the proximal branch 22, which enables consequently the nut 4 to run therethrough, without this nut 4 resting against the branch 22.

The distal branch 21 comprises a hole of diameter smaller than that of the nut 4, so that this nut 4 rests, when screwed on the stud 6, solely against this distal branch 21.

The nut 5 also exhibits a circular external form and has a diameter greater than that of the hole 27, so that it rests against the branch 22 when clamped around the stud 6. It therefore clamps both branches 21, 22 and immobilises the linking rod 2.

For their rotational manoeuvres, the nuts 4 and 5 each comprise four radial notches 30, which can accommodate the complementary teeth of a screwing tool.

Figure 7:
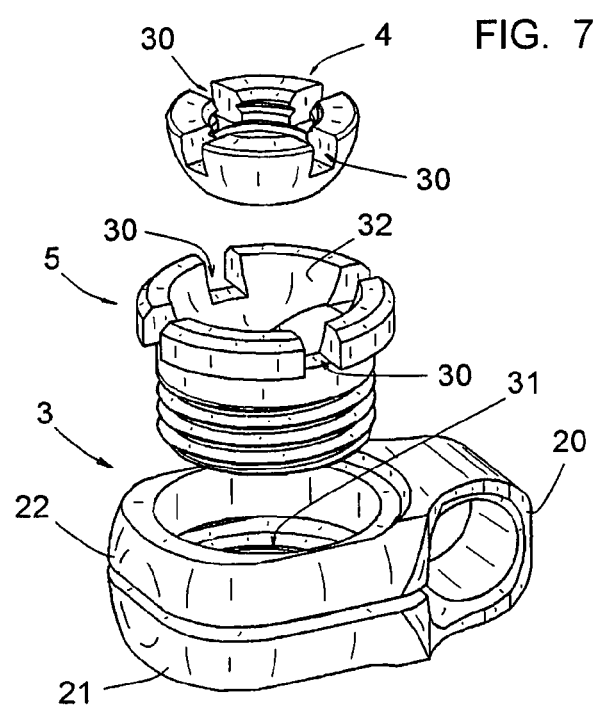
FIG. 7 is a perspective view of a connecting part, of a nut and of a screw according to a third embodiment.
Figure 8:
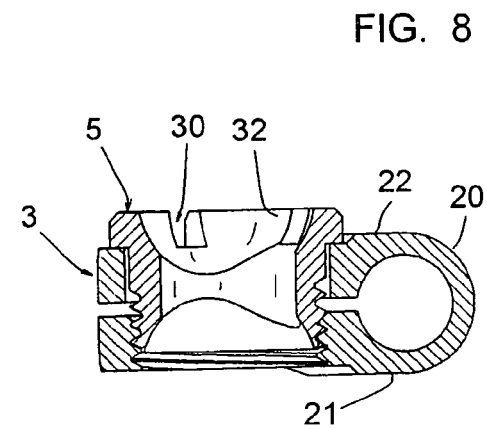
FIG. 8 is a sectional view of this connecting part and of this screw.

FIGS. 7 and 8 show a connecting part 3, a nut 4 and a screw 5 according to the third embodiment.

In such a case, the distal branch 21 exhibits a tapered bore 31 for screwing the screw 5 and the proximal branch 22 exhibits a hole of diameter greater than the threaded body of this screw 5 but smaller than the diameter of the head of this screw 5.

The nut 4 has an external form as a portion of a sphere and comprises notches 30 for its rotational manoeuvre.

The screw 5 exhibits a threaded body for screwing in the tapered bore 31 and a circular screw head resting against the proximal branch 22. This head comprises four notches 30 and a cavity 32 as a portion of a hollow sphere, intended for accommodating the nut 4.

The screw 5 is tubular and exhibits an axial bore of diameter greater than that of the stud 6, so that the connecting part 3 may, when it includes the screw 5, be engaged on this stud 6.

Thanks to the screw 5, the connecting part 3 may be clamped on the linking rod 2 then be engaged on the stud 6 and be clamped on the anchoring member 1 using the nut 4.

Figure 9:
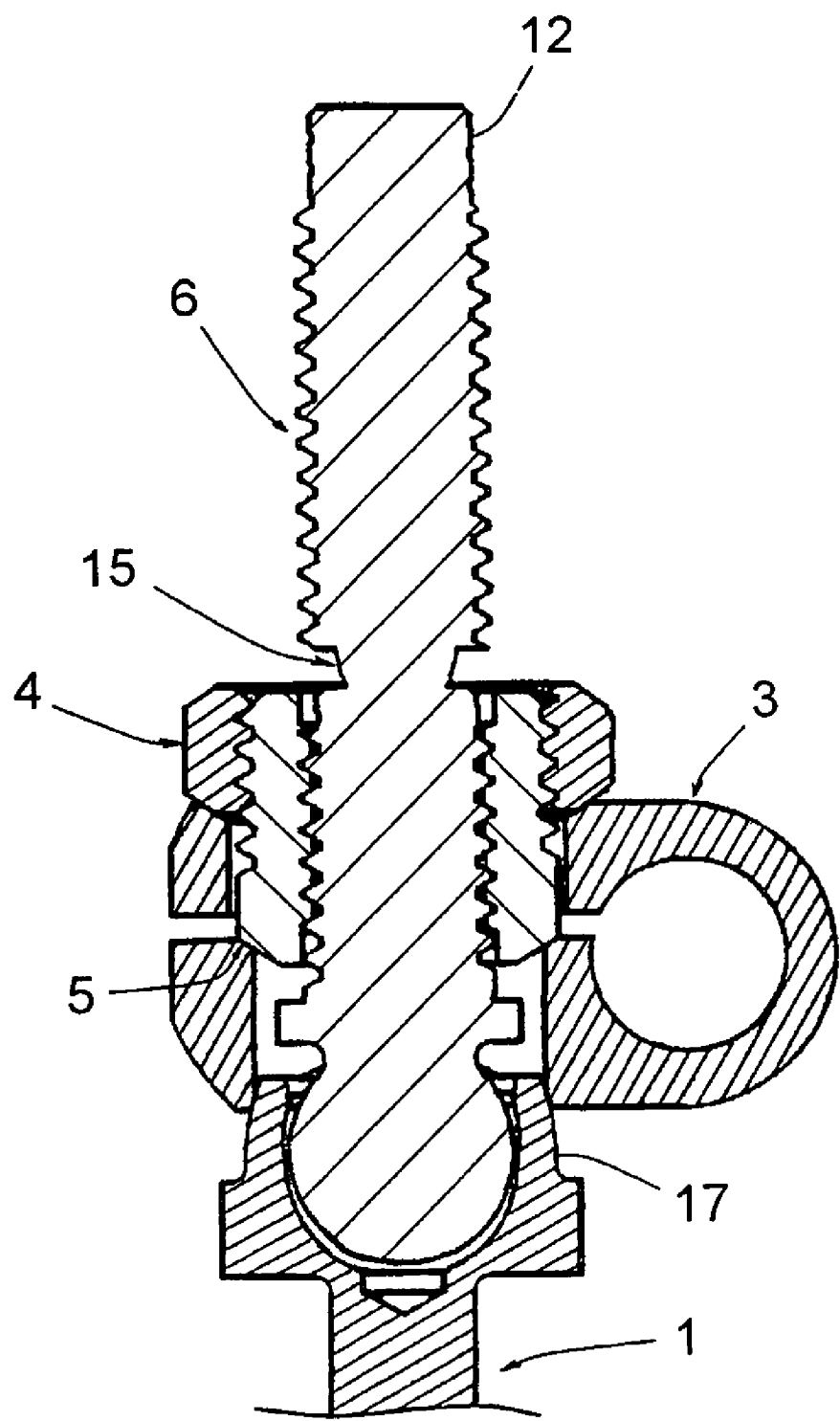
FIG. 9 is a partial view of a polyaxial pedicular screw, of a connecting part in cross-section and of two nuts included in such equipment, according to a third embodiment.

FIG. 9 shows an embodiment in which the nut 4 has a threaded upper portion on which can be screwed the nut 5.

As shown by the foregoing, the invention provides vertebral osteosynthesis equipment noticeably easier and quicker to implant than any extent equipment, enabling to facilitate significantly the determination of the form to confer the linking rod(s) and enabling perfect clamping of a linking rod, as well as to resist the repeated loads inflected to this type of equipment.

It is obvious that the invention is not limited to the embodiment described above for exemplification purposes but that it extends to all the embodiments covered by the claims appended therein.

The invention claimed is:

1. A vertebral osteosynthesis equipment, comprising:
   bony anchoring members;
   one or two linking rods (2), intended to be connected to the bony anchoring members and to be attached to the vertebrae by dint thereof; and
   a connecting part (3) for connecting the linking rod(s) (2) to the bony anchoring members, at least one bony anchoring member including a proximal threaded stud (6) and a first fastening nut (4) intended to be screwed on the proximal threaded stud (6) for assembling the connecting part (3) thereon, and the connecting part (3) including a second fastening nut (5) engaged on the proximal threaded stud (6) of said at least one bony anchoring member coaxially with said first fastening nut (4), wherein
   said connecting part (3) comprises a rounded section (20) intended for hugging the linking rod (2) and two parallel distal and proximal branches (21, 22) drilled with holes for engagement on the proximal threaded stud (6) of said at least one bony anchoring member (1), the two parallel distal and proximal branches (21, 22) being laid out for being clamped in order to clamp said rounded section (20) around the at least one linking rod (2),
   said second fastening nut (5) has threaded means enabling to clamp the two parallel distal and proximal branches (21, 22) of the connecting part (3) so as to immobilize the linking rod (2) with respect to the connecting part (3),
   said distal branch of the connector includes a proximal face opposite the proximal branch and said first fastening nut being introduced in the hole of the proximal branch until reaching and resting directly on the proximal face of the distal branch,
   said second fastening nut resting directly on the proximal branch of the connector,
   said first and second fastening nuts are separated elements, and
   said first fastening nut is completely tightened when bearing on the distal branch.

2. The vertebral osteosynthesis equipment according to claim 1, wherein
   the proximal branch (22) of the connecting part (3), i.e. the furthermost from the vertebrae after implantation, comprises a hole (27) for letting said first fastening nut (4) therethrough, so that said first fastening nut (4) rests, when screwed on said proximal threaded stud (6), on the distal branch (21) of the connecting part (3), and said second fastening nut (5) exhibits a diameter greater than that of the hole (27), so that said second fastening nut (5) rests, when screwed on said proximal threaded stud (6), on the proximal branch (22) of the connecting part (3), thereby clamping the two parallel distal and proximal branches (21, 22) and therefore immobilizing the linking rod (2).

3. The vertebral osteosynthesis equipment according to claim 1, wherein the hole (31) of the distal branch (21) of the connecting part (3), i.e. the closest of the vertebrae after implantation, is tapered;

said second fastening nut (5) is in the form of a tubular screw, which may be screwed in the hole (31) of the distal branch (21) and rest against the proximal branch (22) for clamping both branches (21, 22), an axial bore of the screw having a diameter greater than that of the proximal threaded stud (6) so as not to oppose the engagement of the connecting part (3), thus equipped with said second fastening nut (5), on the proximal threaded stud (6), and said first fastening nut (4) is in the form of a nut which may rest against a head of the screw formed by said second fastening nut (5), for assembly of the connecting part (3) on the proximal threaded stud (6).

4. The vertebral osteosynthesis equipment according to claim 1, wherein the proximal branch (22) of the connecting part (3) is shorter than the distal branch (21) and comprises a scalloping (27) at of its free end;

the first and second fastening nuts (4, 5) which may be screwed on the proximal stud (6) of the corresponding anchoring member (1), scalloping (27) having dimensions greater than first fastening nut, to enable the first fastening nut (4) to rest, when being clamped, against the distal branch (21) and to clamp the branch (21) against a proximal zone (17) of a portion (7) of the anchoring member engaged with the vertebra until the connecting part (3) is locked with respect to said proximal stud (6), and said scalloping (27) having dimensions smaller than those of the second fastening nut, to enable the second fastening nut (5) to rest, when being clamped, against the proximal branch (22) and to bring both branches (21, 22) closer to one another in order to immobilize the linking rod (2) in said rounded section (20) of the connecting part (3).

5. The vertebral osteosynthesis equipment according to claim 1, wherein a proximal zone of a portion (7) of the bony anchoring member configured to be engaged with the vertebra comprises a hemispherical wall (17) and in that the distal branch (21) exhibits a hemispherical distal cavity (25) coaxial to said hole and of a diameter greater than that of the wall (17).

6. The vertebral osteosynthesis equipment according to claim 1, wherein the proximal threaded stud (6) exhibits a threaded proximal rod (12) which enables the assembly of an extension piece.

7. The vertebral osteosynthesis equipment according to claim 1, wherein the proximal threaded stud (6) exhibits a threaded cylindrical portion (10) which exhibits a zone (15) of reduced diameter, enabling to break a proximal portion of said threaded cylindrical portion (10).

8. The vertebral osteosynthesis equipment according to claim 1, wherein the first fastening nut has a threaded upper portion on which can be screwed the second fastening nut (5).

9. The vertebral osteosynthesis equipment according to claim 1, wherein the bony anchoring members are at least one of pedicular screws (1) or hooks.

10. The vertebral osteosynthesis equipment according to claim 1, wherein the first and second fastening nut (4, 5) are screwable on said proximal threaded stud (6).

11. A vertebral osteosynthesis equipment, comprising:
bony anchoring members;
one or two linking rods (2), configured to be connected to the bony anchoring members and to be attached to the vertebrae by dint thereof; and
a connecting part (3) for connecting the one or two linking rods (2) to the bony anchoring members, at least one bony anchoring member including a proximal threaded stud (6) and a first threaded nut (4) intended to be screwed on the proximal threaded stud (6) for assembling the connecting part (3) thereon, and the connecting part (3) including a second threaded nut (5) engaged on the proximal threaded stud (6) of said at least one bony anchoring member coaxially with said first threaded nut (4), wherein
said connecting part (3) comprises a rounded section (20) configured for hugging the one or two linking rods (2) and two parallel distal and proximal branches (21, 22) drilled with holes for engagement on the proximal threaded stud (6) of said at least one bony anchoring member, the two branches (21, 22) being laid out for being clamped in order to clamp said rounded section (20) around at least one of the one or two linking rods (2), and
said second threaded nut (5) is configured to clamp both distal and proximal branches (21, 22) of the connecting part (3) so as to immobilize the linking rod (2) with respect to the connecting part (3),
said distal branch of the connector includes a proximal face opposite the proximal branch and said first fastening nut being introduced in the hole of the proximal branch until reaching and resting directly on the proximal face of the distal branch,
said second fastening nut resting directly on the proximal branch of the connector,
said first and second fastening nuts are separated elements, and
said first fastening nut is completely tightened when bearing on the distal branch.

12. The vertebral osteosynthesis equipment according to claim 11, wherein the proximal branch (22) of the connecting part (3), i.e. the furthermost from the vertebrae after implantation, comprises a hole (27) for letting said first threaded nut (4) therethrough, so that said first threaded nut (4) rests, when screwed on said proximal threaded stud (6), on the distal branch (21) of the connecting part (3), and said second threaded nut (5) exhibits a diameter greater than that of the hole (27), so that said second threaded nut (5) rests, when screwed on said proximal threaded stud (6), on the proximal branch (22) of the connecting part (3), thereby clamping the two parallel distal and proximal branches (21, 22) and therefore immobilizing the linking rod (2).

13. The vertebral osteosynthesis equipment according to claim 11, wherein the hole (31) of the distal branch (21) of the connecting part (3), i.e. the closest to the vertebrae after implantation, is tapered;

said threaded nut (5) is a tubular screw, which may be screwed in the hole (31) of the distal branch (21) and rest against the proximal branch (22) for clamping the two parallel distal and proximal branches (21, 22), an axial bore of the screw having a diameter greater than that of the proximal threaded stud (6) so as not to oppose the engagement of the connecting part (3), thus equipped with said second threaded nut (5), on the proximal threaded stud (6), and said first threaded nut (4) is a nut which may rest against a head of the screw formed by said second threaded nut (5), for assembly of the connecting part (3) on the proximal threaded stud (6).

14. The vertebral osteosynthesis equipment according to claim 11, wherein the proximal branch (22) of the connecting part (3) is shorter than the distal branch (21) and comprises a scalloping (27) at its free end;

the first and second threaded nuts (4, 5) may be screwed on the proximal stud (6) of the corresponding bony anchoring member (1), scalloping (27) having dimensions greater than that of the first threaded nut (4), to enable the first threaded nut (4) to rest, when being clamped, against the distal branch (21) and to clamp the distal branch (21) against a proximal zone (17) of a portion (7) of an anchoring member configured to be engaged with the vertebra until the connecting part (3) is locked with respect to said proximal threaded stud (6), and said scalloping (27) having dimensions smaller than those of the second nut (5) which is part of said second threaded nut (5), to enable the second threaded nut (5) to rest, when being clamped, against the proximal branch (22) and to bring the two parallel distal and proximal branches (21, 22) closer to one another in order to immobilize the linking rod (2) in said rounded section (20) of the connecting part (3).

15. The vertebral osteosynthesis equipment according to claim 11, wherein a proximal zone of a portion (7) of the anchoring member (1) configured to be engaged with the vertebra comprises a hemispherical wall (17) and in that the distal branch (21) exhibits a hemispherical distal cavity (25) coaxial to said hole and of diameter greater than that of the hemispherical wall (17).

16. The vertebral osteosynthesis equipment according to claim 11, wherein the proximal threaded stud (6) exhibits a threaded proximal rod (12) which enables the assembly of an extension piece.

17. The vertebral osteosynthesis equipment according to claim 11, wherein the proximal threaded stud (6) exhibits a threaded cylindrical portion (10) which exhibits a zone (15) of reduced diameter, enabling to break a proximal portion of said threaded cylindrical portion (10).

18. The vertebral osteosynthesis equipment according to claim 11, wherein the first threaded nut (4) has a threaded upper portion on which can be screwed the second threaded nut (5).

19. The vertebral osteosynthesis equipment according to claim 11, wherein the bony anchoring members are at least one of pedicular screws (1) or hooks.

* * * * *